United States Patent
Rau

(10) Patent No.: US 8,828,706 B2
(45) Date of Patent: Sep. 9, 2014

(54) USE OF CARBONATES FOR BIOLOGICAL AND CHEMICAL SYNTHESIS

(71) Applicant: Lawrence Livermore National Security, LLC, Livermore, CA (US)

(72) Inventor: Gregory Hudson Rau, Castro Valley, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 0 days.

(21) Appl. No.: 13/797,434

(22) Filed: Mar. 12, 2013

(65) Prior Publication Data

US 2014/0004596 A1 Jan. 2, 2014

Related U.S. Application Data

(60) Provisional application No. 61/665,249, filed on Jun. 27, 2012.

(51) Int. Cl.
| | |
|---|---|
| C01B 31/20 | (2006.01) |
| C12N 1/04 | (2006.01) |
| C12M 1/107 | (2006.01) |
| C12M 1/34 | (2006.01) |

(52) U.S. Cl.
CPC .............. C12M 41/34 (2013.01); C12M 41/32 (2013.01)
USPC .......................................... 435/243; 423/438

(58) Field of Classification Search
CPC ...... C12M 43/02; C12M 43/04; C12M 43/06; B01J 21/18; C10J 2300/0916; C10J 2300/0923; B09B 3/00; C04B 2/00; C04B 22/00; C12N 1/12; Y02C 10/00; Y02C 10/14; F17C 2223/00; F17C 1/00
See application file for complete search history.

(56) References Cited

U.S. PATENT DOCUMENTS

| | | | |
|---|---|---|---|
| 6,209,256 B1 * | 4/2001 | Brittin et al. .................... 43/107 |
| 6,890,497 B2 | 5/2005 | Rau et al. | |
| 7,655,193 B1 | 2/2010 | Rau et al. | |
| 2009/0038955 A1 | 2/2009 | Rau | |
| 2010/0107487 A1 * | 5/2010 | Holland ........................... 47/1.4 |
| 2010/0297749 A1 * | 11/2010 | Aravanis et al. ........... 435/289.1 |

FOREIGN PATENT DOCUMENTS

CN 201240853 Y * 5/2009 .............. C01B 31/20

OTHER PUBLICATIONS

The Royal Society, Policy Document. 2005. Annex 1: A brief account of measures of acidity such as pH, and the acid-base chemistry of the $CO_2$-carbonate system in the sea. In: Ocean acidifcation due to increasing atmospheric carbon dioxide. The Royal Society, Ed: The Clyvedon Press Ltd., Cardiff, UK, 2005, pp. 43-44.*
Calcium Carbonate. Datasheet [online]. PubChem, National Center for Biotechnology Information, U.S. National Library of Medicine [retrieved on Nov. 1, 2013]. Retrieved from the Internet: <URL: http://pubchem.ncbi.nlm.nih.gov/summary/summary.cgi?cid=10112&loc=ec_rcs>. p. 1.*
English translation of: Zheng, Lin et al. Self-control type carbon dioxide generation apparatus. CN 201240853(Y). May 20, 2009. pp. 1-8; specif. pp. 1-2 and 5.*
L. Brennan and P. Owende, "Biofuels from microalgae—A review of technologies for production, processing, and extractions of biofuels and co-products," Renewable and Sustainable Energy Reviews, 14:557-577 (2010).
Morse et al., "Calcium carbonate formation and dissolution," Chem. Rev. 107: 342-381 (2007).
J. Kuss and B. Schneider, "Chemical enhancement of the $CO_2$ gas exchange at a smooth seawater surface," Marine Chemistry 91: 165-174 (2004).

* cited by examiner

Primary Examiner — John S Brusca
Assistant Examiner — Sharon M Papciak
(74) Attorney, Agent, or Firm — Eddie E. Scott

(57) ABSTRACT

A system of using carbonates, especially water-insoluble or sparing soluble mineral carbonates, for maintaining or increasing dissolved inorganic carbon concentrations in aqueous media. In particular, the system generates concentrated dissolve inorganic carbon substrates for photosynthetic, chemosynthetic, or abiotic chemical production of carbonaceous or other compounds in solution. In some embodiments, the invention can also enhance the dissolution and retention of carbon dioxide in aqueous media, and can produce pH buffering capacity, metal ions, and heat, which can be beneficial to the preceding syntheses.

28 Claims, 8 Drawing Sheets

USE OF CARBONATES FOR BIOLOGICAL AND CHEMICAL SYNTHESIS

CROSS-REFERENCE TO RELATED APPLICATIONS

This application claims benefit under 35 U.S.C. §119(e) of U.S. Provisional Patent Application No. 61/665,249 filed Jun. 27, 2012 entitled "Mineral Carbon Sources for Chemical and Biochemical Synthesis," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to chemical and biochemical synthesis and more particularly to the use of carbonates for chemical and biochemical synthesis.

2. State of Technology

Autotrophic, aquatic organisms are commonly cultured to produce a range of products including food, feed, and chemical feedstocks. Considerable interest has also recently focused on the mass culture of such organisms for the direct or indirect production of fuels (biofuels). Because the preceding organisms usually synthesize organic compounds from inorganic carbon dissolved in the growth media, an adequate source of such carbon is critical for space- and volume-efficient biological production of end products. The internal biological demand for inorganic carbon can outstrip that which can be supplied via simple air equilibration with the media. This is commonly rectified by elevating the dissolved inorganic concentration in the media via equilibration with gas containing elevated $CO_2$ and/or the addition of synthetic, soluble carbon salts such as sodium carbonate or bicarbonate. Sources of concentrated $CO_2$ gas include commercial tank gas, $CO_2$ gas generators, and waste $CO_2$, in most cases derived from the combustion of fossil fuels. Use of such $CO_2$ sources therefore make the resulting biofuels dependent on fossil fuels, defeating one of the primary rationales for biofuel production. Furthermore, bubbling of gas into a solution is a relatively inefficient way of producing dissolved inorganic carbon, which can result in the loss of significant quantities of undissolved $CO_2$ to air. The use of commercially produced carbon salts, in particular sodium carbonate or bicarbonate, as a carbon source must be limited because of their relatively high production cost and fossil carbon footprint.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Embodiments of the present invention provide a system for maintaining or increasing the dissolved inorganic carbon concentration in aqueous media including the steps of contacting and reacting a carbonate with an acid, collecting the $CO_2$ so generated, and contacting the $CO_2$ with said aqueous media thereby maintaining or increasing the dissolved inorganic carbon concentration in the aqueous media for biotic synthesis.

Embodiments of the present invention also provide an apparatus for maintaining or increasing the dissolved inorganic carbon concentration in aqueous media including a vessel in which carbonate is reacted with an acid, thus producing $CO_2$, a system of collecting and transporting said $CO_2$ to said aqueous media, and a system of contacting and reacting said $CO_2$ with said aqueous media thereby maintaining or increasing said dissolved inorganic carbon concentration in said aqueous media for biotic synthesis.

Other embodiments provide systems to generate soluble carbon salts from otherwise insoluble, inexpensive mineral carbonates, which are then added to culture media as a carbon substrate for subsequent biological synthesis. Such embodiments can also provide low cost pH buffering capacity, alkalinity, metal ions, and heat that can be beneficial for such synthesis. The conversion of $CO_2$ gas to dissolved inorganic carbon is also hastened by the aforementioned maintenance or elevation of pH and alkalinity. Thus, embodiments of the present invention can provide more efficient, more beneficial, and less costly ways of adding, maintaining, or elevating dissolved inorganic carbon in aqueous media, and in some cases also reduce fossil fuel dependences in supplying such dissolved inorganic carbon.

The present invention may also be useful for efficiently and inexpensively providing elevated dissolved inorganic carbon concentrations and beneficial aqueous chemical conditions for abiotic, chemical synthesis of organic or inorganic compounds.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1A:
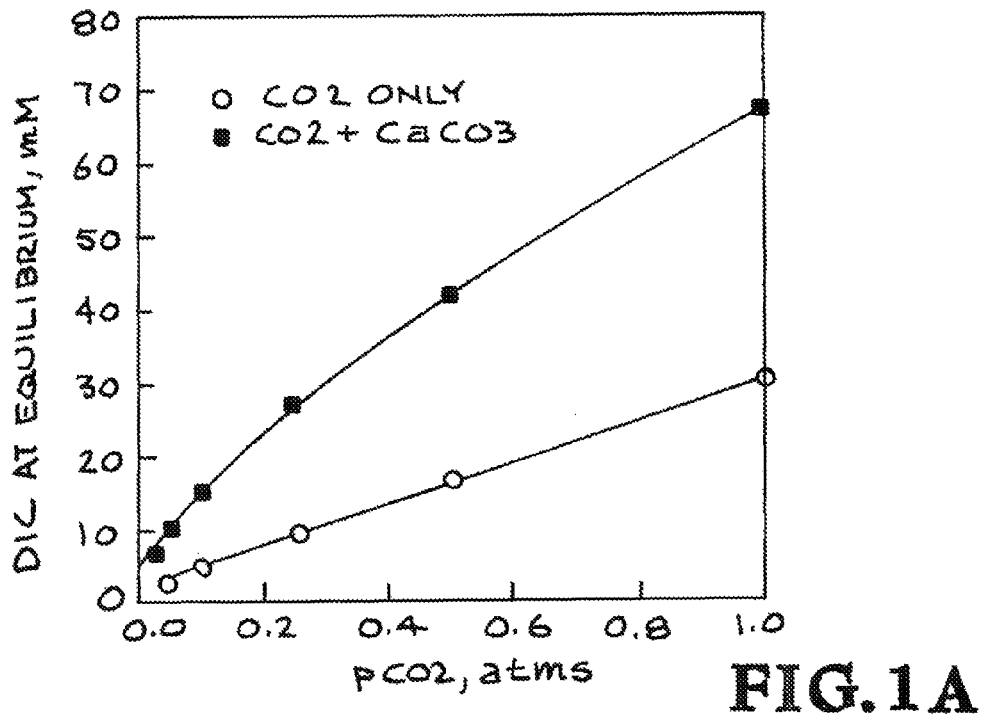
FIG. 1 is a graph illustrating solution DIC (A) and pH (B) as a function of equilibrium $pCO_2$ in seawater and in seawater also equilibrated with excess $CaCO_{3(s)}$. Initial: $pCO_2=3.9\times10^{-4}$ atmosphere (atms; air $CO_2$), DIC=2.0 mM, alkalinity =2.35 mM, pH=8.05, salinity=35 ppt, temperature=25° C., total gas pressure=1 atms.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Elevated dissolve inorganic carbon (DIC) concentrations are often required to maintain high density aquatic autotrophic organism cultures, for example as used in the biosynthesis of products such as food, food additives, pharmaceuticals, animal feed, and fuels (e.g., Brennan and Owende, 2010). Here DIC is defined as the sum of the concentrations of all forms of dissolved inorganic C in a solution:

$$DIC=[CO_{2(aq)}]+[H_2CO_3]+[HCO_3]+[CO_3^{2-}] \qquad (1)$$

whose abundances relative to each other are dictated by well known, pH-dependent equilibrium reactions. Due to diffusion rate limitations, contact with air (currently 0.039% $CO_2$) can be an inadequate source of such carbon for high-density, high carbon demand biosynthesis. Previously described methods of increasing DIC include aeration of the liquid culture media with gas containing elevated $CO_2$ such as from commercially available tanks, $CO_2$ generators, or waste streams, e.g., flue gas. The addition of soluble inorganic carbon salts such as synthetic sodium carbonate or bicarbonate is also used. However, all of the preceding sources of DIC can be expensive, may have limited availability relative to biosynthesis scale, and unacceptably depress media pH (in the case of $CO_2$ addition). The invention describe here provides ways of alleviating some or all of these limitations by adding DIC and alkalinity from natural, abundant mineral sources of carbon that are otherwise typically insoluble or sparingly soluble in aqueous media.

While calcium and magnesium carbonates are the most abundant carbon containing-compounds on earth, they are usually insoluble in solutions of neutral or higher pH. These carbonates can be dissolved by acidifying with an acid that then releases $CO_2$ gas, e.g.:

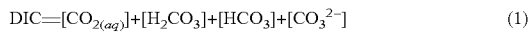

$$CaCO_{3(s)}+H_2SO_{4(aq)} \rightarrow CaSO_{4(aq/s)}+H_2O+CO_{2(g)}\uparrow \qquad (2)$$

The concentrated $CO_2$ gas so produced could be collected and used to equilibrate with aqueous media to elevate its DIC concentration using carbon thus derived from mineral sources. However, a potential negative in doing this is the cost of the acid used for the reaction and the fossil $CO_2$ footprint of the acid's production. Also, the addition of $CO_2$ to media is often an inefficient means of elevating DIC (undissolved $CO_2$ can easily escape from solution), and dissolution of the $CO_2$ can undesirably depress media pH. Use or disposal of the Ca salt and water formed in reaction 2 is an additional concern.

A second and preferred way of generating DIC from mineral carbonate is to react the carbonate with carbonic acid, $H_2CO_3$, e.g.:

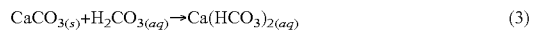

$$CaCO_{3(s)}+H_2CO_{3(aq)} \rightarrow Ca(HCO_3)_{2(aq)} \qquad (3)$$

In this case rather than generating $CO_2$ gas, bicarbonate ions balanced in solution by calcium or other metal ions are produced, resulting in an end product that only exists in dissolved rather than in gaseous form, and can therefore more directly and efficiently contribute to media DIC.

Carbonic acid can be spontaneously formed via $CO_2$ and water contacting:

$$CO_{2(g)}+H_2O \rightarrow H_2CO_{3(aq)} \qquad (4)$$

Indeed, combining reaction 3 and 4 describes a mechanism whereby excess atmospheric $CO_2$ is naturally (but slowly) consumed at global scales (carbonate weathering):

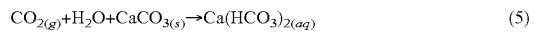

$$CO_{2(g)}+H_2O+CaCO_{3(s)} \rightarrow Ca(HCO_3)_{2(aq)} \qquad (5)$$

Ways of accelerating this reaction to hasten $CO_2$ absorption and sequestration have been previously described (Rau and Caldeira, 2005, 2010; Rau, 2009).

Because the end product of reaction 5 only exists in dissolved form, it is clear that the bicarbonate concentration and hence the DIC of the solution in which this reaction is performed is increased. In fact the maximum DIC concentration attainable via both $CO_2$ and $CaCO_3$ equilibration (reaction 5) can be as high as 3 times that possible with $CO_2$ equilibration (reaction 4) alone for a given equilibration $CO_2$ partial pressure (p$CO_2$; FIG. 1A). That is, if culture media DIC is already being supplied via equilibration with elevated $CO_2$ gas, the resulting media DIC will be significantly increased if the gas and water are also equilibrated with a carbonate mineral. Alternatively, by this method as little as ⅓ less gaseous $CO_2$ will be needed to maintain a given DIC level. This can reduce the cost of supplying DIC because the cost of supplying alternative carbon via mineral carbonate can be fraction of the cost of commercially supplied $CO_2$ gas.

Figure 1B:
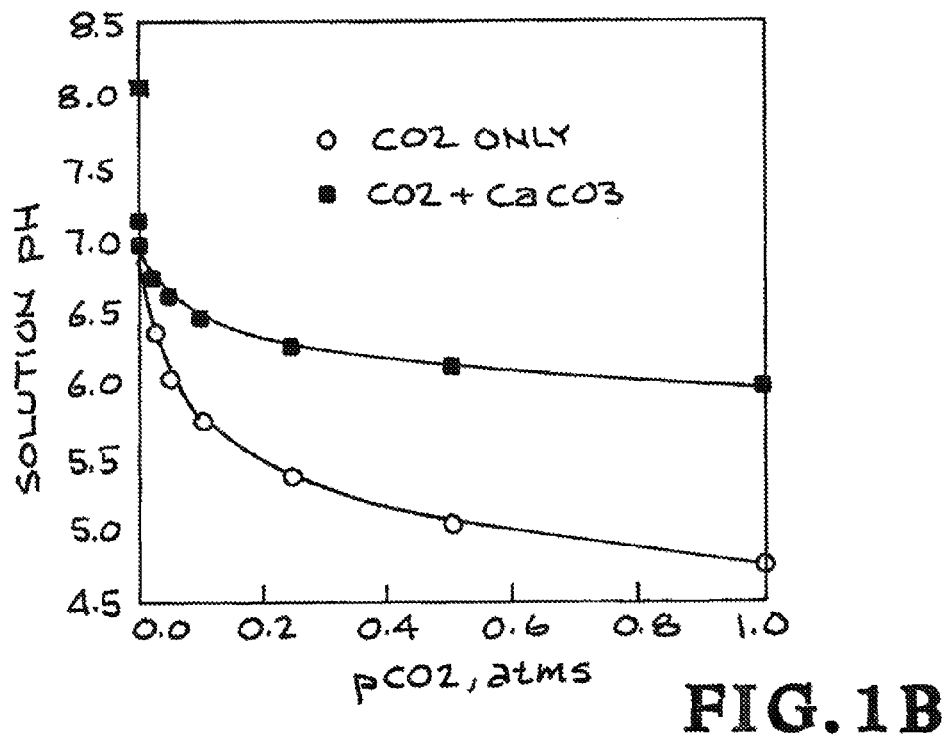
Figure 2A:
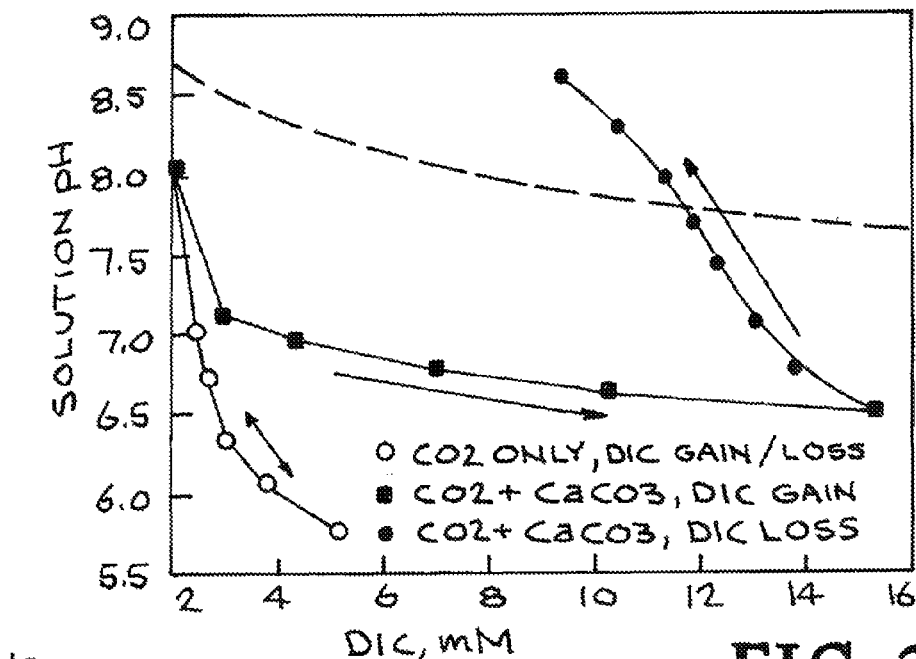
FIG. 2 is a graph illustrating A—Solution DIC versus pH under circumstances where DIC is increased or decreased via $CO_2$ gain/loss alone, or where the solution is also equilibrated with excess $CaCO_{3(s)}$. In each case the solution is seawater with initial conditions as in FIG. 1, and where equilibrium $pCO_2$ varies from $3.9\times10^{-4}$ atms (air) to 0.1 atms. Dashed line denotes boundary above which $CaCO_{3(s)}$ can be expected to precipitate from seawater. Arrows denote trajectories during $CO_2$ gain or loss. B—The enhancement of the $CO_2$ uptake rate via reaction 6 relative to reaction 4 under conditions identical to A.

The formation of $Ca(HCO_3)_{2(aq)}$ and its addition to the media also provides pH buffering capacity. For example, as the p$CO_2$ of the solution's equilibrating gas is increased, the resulting pH depression of the solution is greatly attenuated when equilibration with $CaCO_{3(s)}$ also occurs (FIG. 1B). Furthermore, as $CO_2$ is subsequently lost from the solution via biotic uptake or degassing to the atmosphere, solution pH can rise to values above those of initial conditions in the $CaCO_3$ treated solution, in contrast to the case when solution DIC amendment is by $CO_2$ gas addition only (FIG. 2A). These features can be beneficial for subsequent chemical or biosynthetic processes that may be negatively affected by low pH, but require high DIC concentrations.

Such stabilization or elevation of pH and alkalinity is also beneficial for the formation of DIC from $CO_2$ gas. In addition to the $CO_2$ dissolution by hydration with water (reaction 4), $CO_2$ can also be dissolved into solution via reaction with hydroxyl ions, $OH^-$:

$$CO_2+OH^- \rightarrow HCO_3 \qquad (6)$$

Figure 2B:
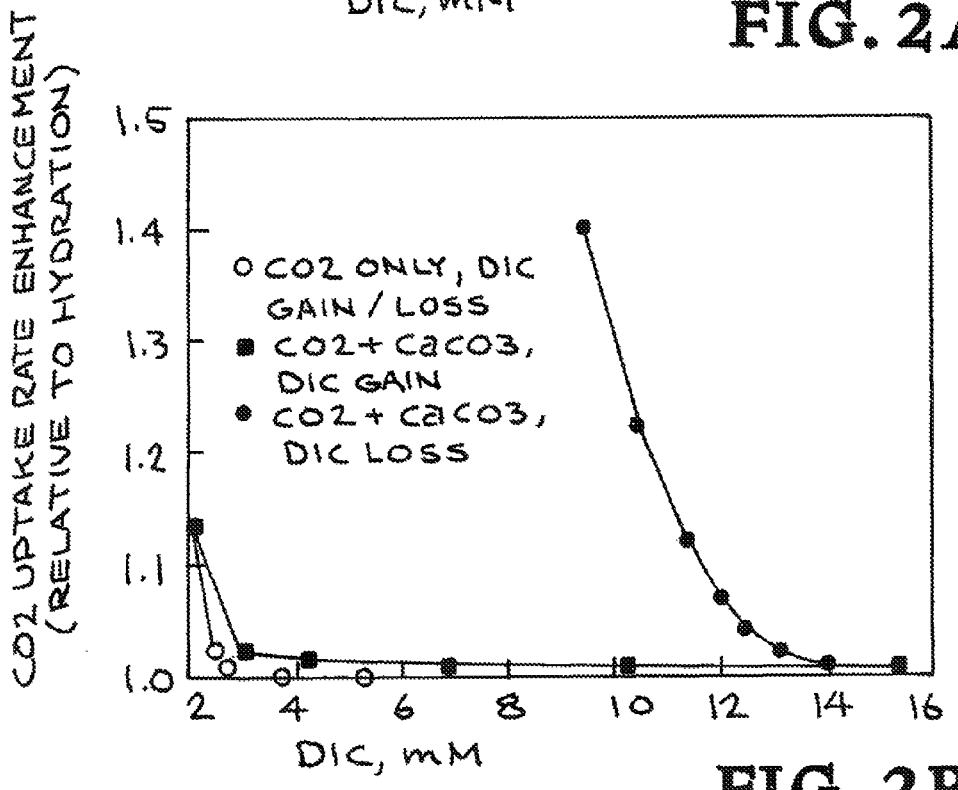
Figure 3:
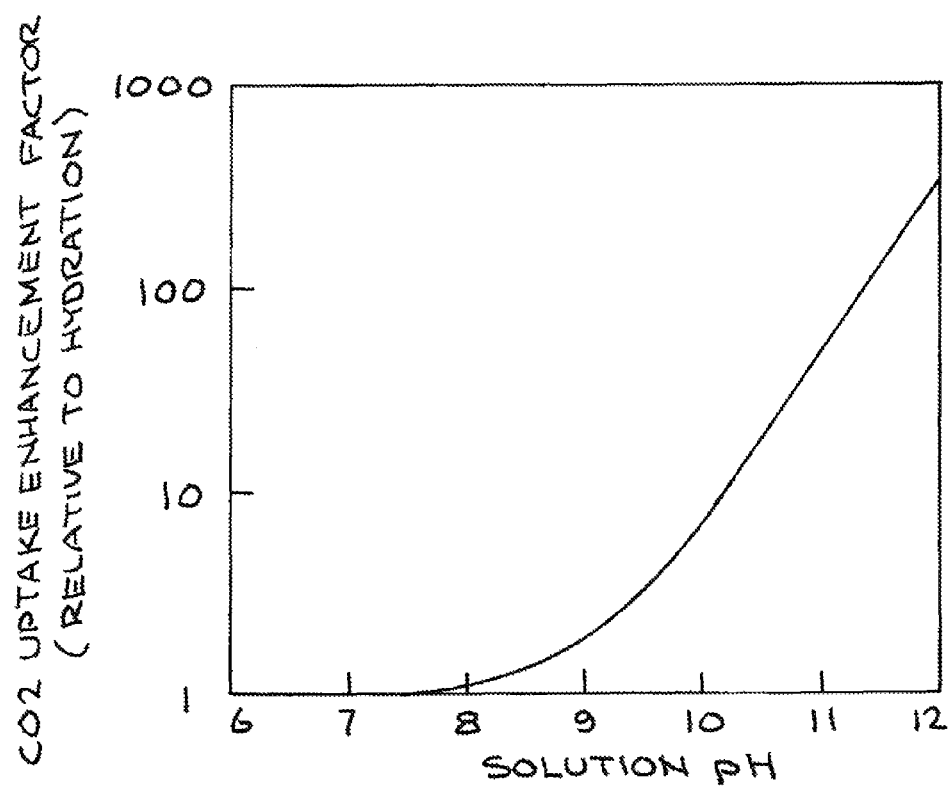
FIG. 3 is a graph illustrating the $CO_2$ uptake rate via hydroxylation relative to hydration in unstirred seawater as a function of solution pH.

Because [OH⁻] increases in aqueous solutions with increasing pH, maintenance of pH above approximately 7.5 will hasten and make more efficient DIC formation from $CO_2$ gas. The effect of pH on the rate of reaction 6 relative to reaction 4 is shown in FIG. 3. Because the addition of $CO_2$ gas alone to unbuffered solutions significantly depresses pH and [OH⁻], methods of buffering and minimizing such pH change as offered by this invention are beneficial where $CO_2$ gas is used as a DIC source in aqueous media. This includes the use of dilute $CO_2$ sources such as found in air, where the speed of dissolution may be greatly enhanced by the invention, thus circumventing the need for more concentrated, more expensive, and/or more fossil-fuel-dependent $CO_2$ sources for DIC amendment. An example of such $CO_2$ uptake enhancement is shown in FIG. 2B.

Carbonate Sources

Any natural or synthetic metal carbonate containing the $CO_3^-$ moiety may be used for the process. However, for reasons of cost and availability, the use of: 1) calcite ($CaCO_3$) for example as contained in limestone, marble, or dolomite, 2) aragonite ($CaCO_3$; e.g., shell material or sedimentary deposits), or 3) magnesite ($MgCO_3$; e.g., dolomite) are preferred. Such carbonate sources are typically insoluble or sparingly soluble in water at pH>7 and therefore not thought of as relevant sources of DIC. This invention provides means of dissolving such carbonates thus allowing their constituents to participate in subsequent aqueous chemical and biochemical reactions.

Forms and Utilization of DIC Supplied

While the principle form of dissolved carbon initially generated by the invention is either $CO_{2(aq)}$ and/or $HCO_3^-$, once in solution these compounds can be converted via equilibrium reactions to other forms of DIC depending on solution pH (eq 1). However, at near neutral pH the dominant form of DIC is $HCO_3^-$. Biosynthetic processes utilize $CO_2$ or $HCO_3^-$, or both. Reports of direct biological utilization of $CO_3^{2-}$ are controversial. Thus, if an organism exclusively uses $CO_2$ as a carbon source, the addition of $HCO_3^-$ to the organism's growth media can still be beneficial due to $CO_{2(aq)}$ resupply via equilibration with $HCO_3^-$. Organisms often use carbonic anhydrase to hasten such equilibration and hence $CO_2$ formation. Nevertheless, as biosynthesis proceeds and $CO_2$ is consumed, the pH of the solution will rise via loss of acidity supplied by $CO_2$ (FIG. 2A). At pH>9 the dominant form of DIC becomes $CO_3^{2-}$ and the equilibrium-dictated proportion of DIC composed of dissolved $CO_2$ is greatly diminished. Those organisms dependent on $CO_2$ as a carbon substrate can thus become carbon limited unless they can efficiently produce $CO_2$ from still abundant $HCO_3^-$ or can switch to direct $HCO_3^-$ utilization. The pH of culture media can be adjusted to optimize the abundance of specific forms of DIC for biosynthesis by the addition of acids, buffers, or chemical bases to the growth media.

If solution/media pH rises, the concentration of $CO_3^{2-}$ will also rise, ultimately saturating the solution with, for example $CaCO_{3(aq)}$, potentially leading to the precipitation of $CaCO_{3(s)}$ and thus a plateauing of DIC concentration and alkalinity (Morse et al., 2007; FIG. 2A). The same would hold true for $MgCO_{3(s)}$ formation from solution. Such precipitation can be avoided via: 1) pH reduction, for example by adding additional $CO_2$, increasing carbonic acid formation, depressing pH, and thus lowering [$CO_3^{2-}$], and/or by 2) the addition of carbonate precipitation inhibitors to the media, which may include phosphate, magnesium, or organic ions or other chemicals (Morse et al., 2007). As an example, abiotic precipitation of $CaCO_3$ is greatly inhibited in seawater by such chemistry, thus $CaCO_{3(aq)}$ concentrations of as much as 18 times above saturation are possible.

As previously mentioned, the invention's ability to avoid significant pH lowering and hence [OH⁻] depression with the addition of DIC and the ability to effect pH and [OH⁻] elevation as $CO_2$ is consumed or lost enhances the rate at which $CO_2$ will dissolve into solution (FIGS. 2A, 3). This is advantageous for speeding up DIC formation from $CO_2$ gas supplied to the solution, including dilute $CO_2$ gas sources such as air, and it is advantageous for reducing undissolved $CO_2$ gas losses from solution.

Abiotic Synthesis

It is understood that the use of mineral carbonates for DIC production may be beneficial in providing starting compounds or substrates, buffering capacity, metal ions, and/or heat for abiotic, chemical synthesis of organic or inorganic compounds in aqueous media. Such production may include plastics, pharmaceuticals, fuels, and chemical feed stocks.

The present invention is further described and illustrated by a number of examples of systems constructed in accordance with the present invention. Various changes and modifications of these examples will be apparent to those skilled in the art from the description of the examples and by practice of the invention. The scope of the invention is not intended to be limited to the particular examples disclosed and the invention covers all modifications, equivalents, and alternatives falling within the spirit and scope of the invention as defined by the claims. The present invention is further described and illustrated by examples of methods, apparatus and protocols for DIC generation and addition.

Example 1

Acidification of Carbonates—$CO_2$ & DIC Production

Figure 4:
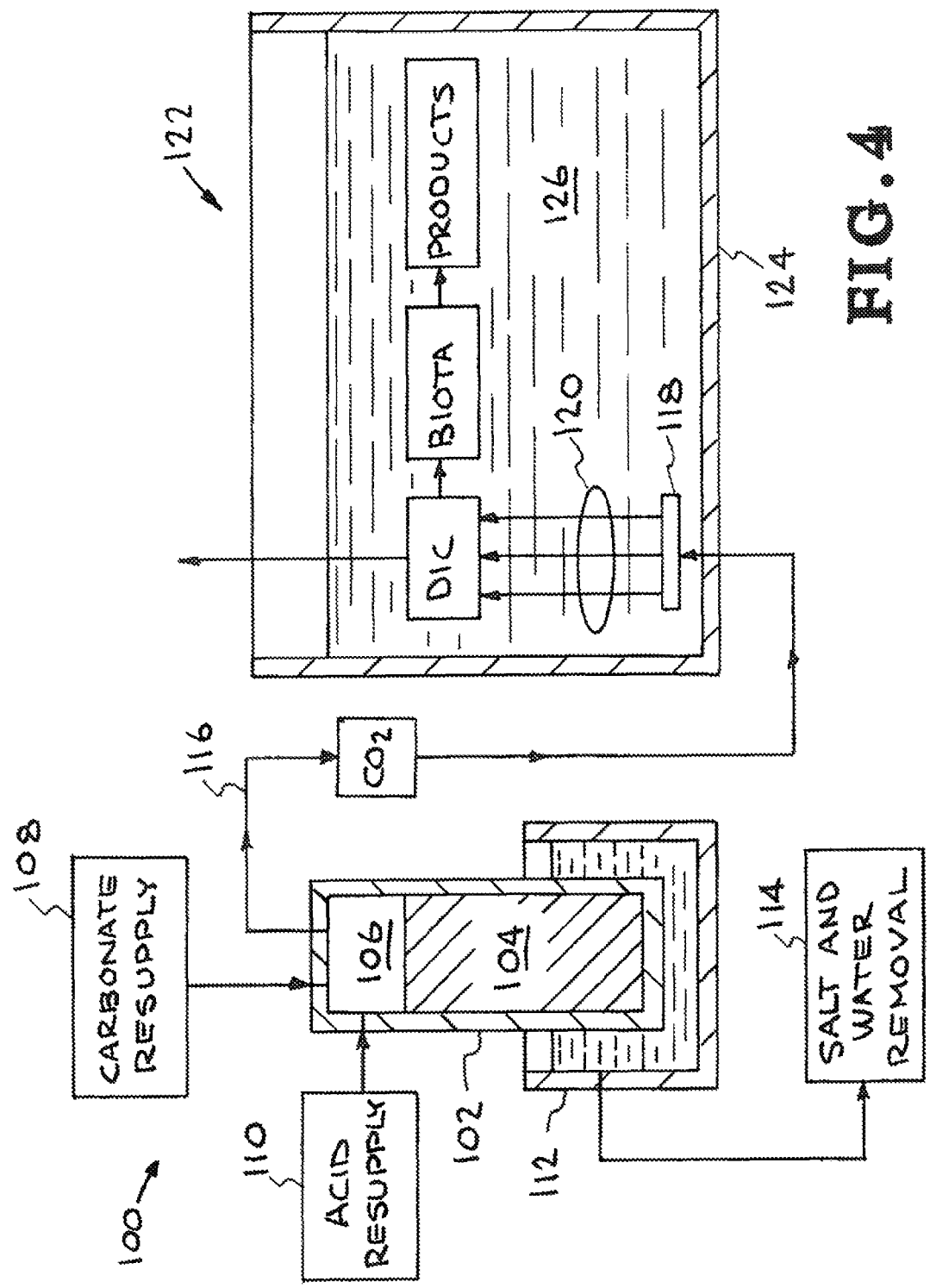
FIG. 4 illustrates an example of acidification of mineral carbonates to generate $CO_2$ followed by DIC production.

Referring to FIG. 4, a system for acidification of mineral carbonates to generate $CO_2$ followed by DIC production is illustrated. A carbonate reactor is designated generally by the reference numeral 100. As illustrated in FIG. 4, crushed limestone is added to a vessel 102 into which dilute sulfuric acid solution 110 is subsequently slowly added. Limestone particles 104 are in the vessel 102 and a system for salt and water removal 114 is provided. The vessel is designed with a headspace 106 that allows the collection of the resulting $CO_2$ gas 116 as it evolves from the solution, and if necessary the vessel is at least partly submerged in the water bath 112 to dissipate heat generated by the exothermic acid reaction with the carbonate. If desired, this waste heat can be used via conventional means to maintain or elevate the temperature of the culture media or can be used for other purposes. Facilities for limestone resupply 108 and spent acid solution (primarily $CaSO_4$ and water) removal are provided.

The gas 116 is piped to a bioreactor 122 containing growth media 126 and biota. A gas diffuser 118 produces a $CO_2$ stream 120 in the media 126 in the vessel 124. This $CO_2$ equilibration 120 elevates media DIC that concurrently or subsequently is then used as a growth media for biosynthesis, either in batch or continuous culture mode. The rate of media recycling, gas flow, and/or quantity of exposed limestone surface area can be used to control DIC concentration relative to DIC utilization or loss.

Example 2

Carbonic Acid & Mineral Bicarbonate Formation

Figure 5:
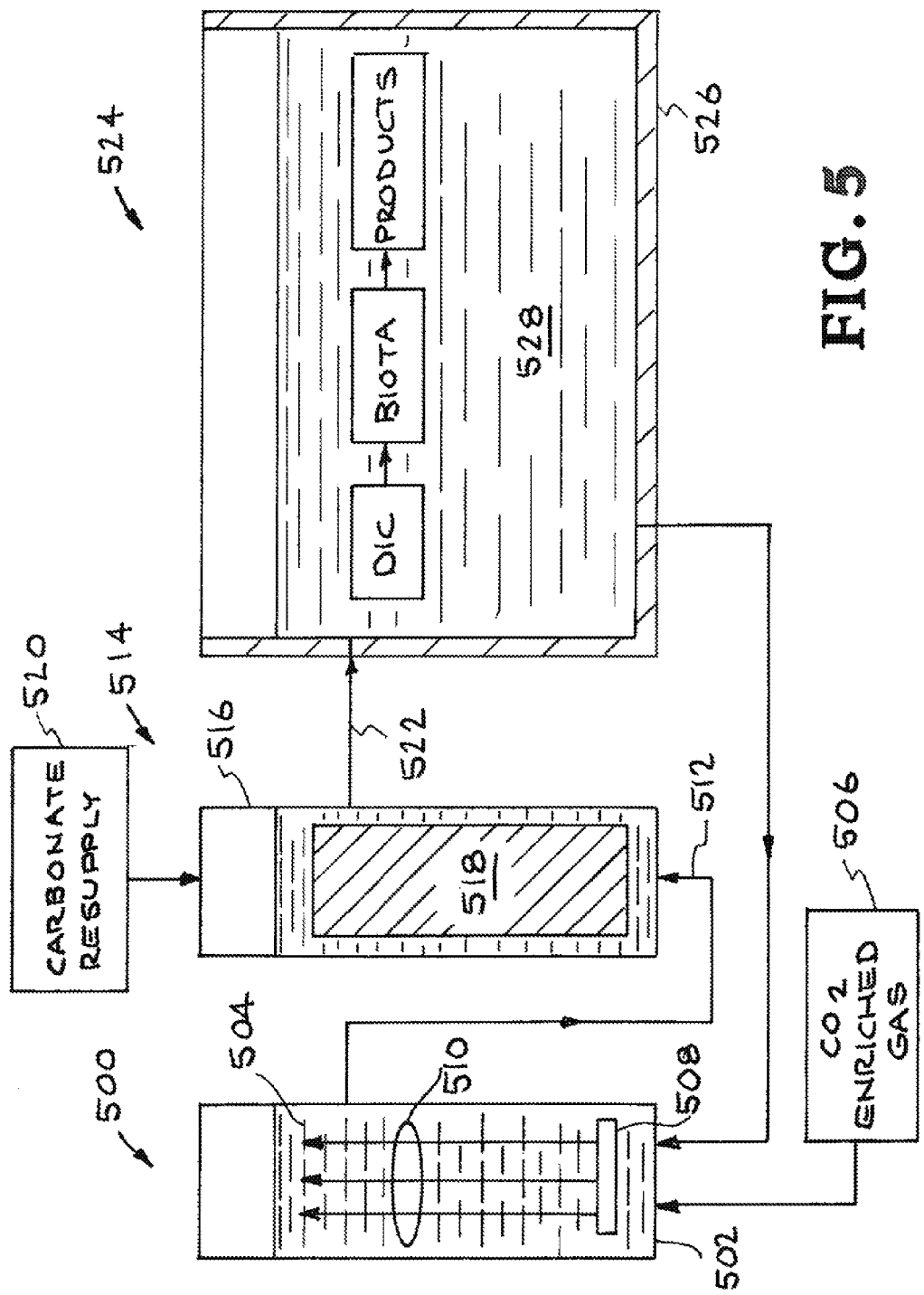
FIG. 5 illustrates an example of sequential carbonic acid and dissolved mineral bicarbonate formation.

Referring to FIG. 5, a system for sequential carbonic acid and dissolved mineral bicarbonate formation is illustrated. As illustrated in FIG. 5, a $CO_2$ reactor 500 receives gas containing $CO_2$ 506 that is bubbled through a vessel 502 containing sporadically or continuously flowing solution media from a bioreactor 524. A diffuser 508 produces a $CO_2$ stream 510 in the solution 504 in the vessel 502. The $CO_2$ partially or fully equilibrates with the solution forming carbonic acid 512.

As illustrated in FIG. 5, a carbonate reactor 514 receives carbonic acid 512. The acidified media 512 is fed into a second vessel 516 containing crushed limestone 518 where the contact between the limestone and the acidified media results in dissolution of some of the limestone, forming calcium bicarbonate in solution 522. A system for carbonate resupply 520 is provided.

The now DIC-enriched media 522 is fed to a third vessel 526 (biosynthesis reactor 524) containing biota and aqueous media 528 where the DIC is used for biosynthesis. As biosynthesis proceeds the media becomes DIC-depleted. The DIC-deplete media is subsequently returned to the first reactor 500 and the cycle repeated. The rate of media recycling, gas flow, $CO_2$ concentration, and/or quantity of exposed limestone surface area can be used to control DIC concentration relative to DIC utilization or loss.

Example 3

Carbonic Acid & Mineral Bicarbonate Formation

Figure 6:
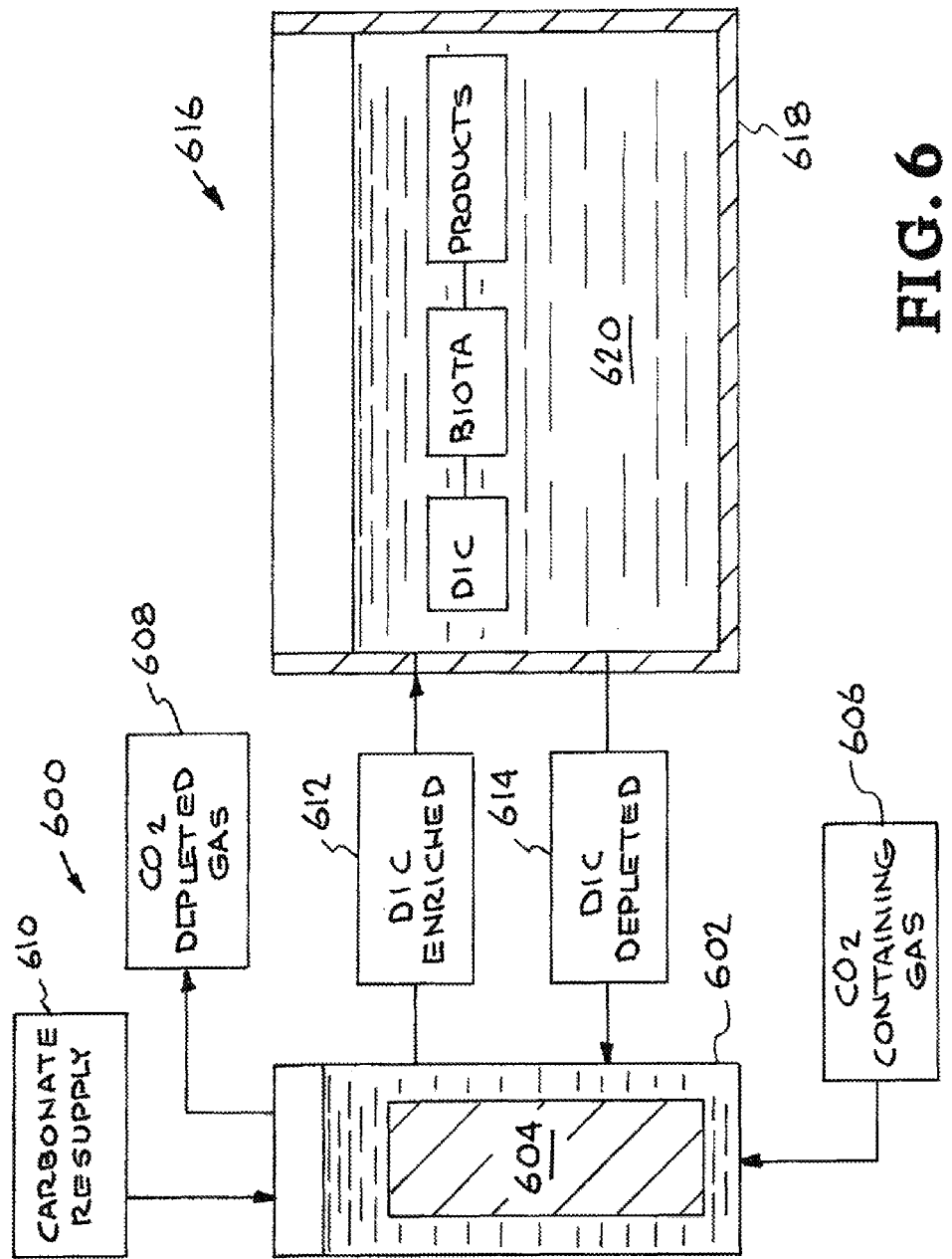
FIG. 6 illustrates an example of integrated carbonic acid and dissolved mineral bicarbonate formation.

Referring to FIG. 6, a system for integrated carbonic acid and dissolved mineral bicarbonate formation is illustrated. In a $CO_2$ and carbonate reactor 600, gas 606 containing $CO_2$ is bubbled through a vessel 602 containing limestone particles 604 and sporadically or continuously flowing solution media from a bioreactor 616. The $CO_2$ partially or fully equilibrates with the solution forming carbonic acid that in turn reacts with at least some of the limestone forming calcium bicarbonate in solution. The now DIC-enriched media 612 is fed to a second vessel 618 (bioreactor 616) containing biota and aqueous media 620 where the DIC is used for biosynthesis. The subsequently DIC-deplete media 614 is returned to the first reactor 600 and the cycle repeated. The rate of media recycling, gas flow, $CO_2$ concentration, and/or quantity of exposed limestone surface area can be used to control DIC concentration relative to DIC utilization or loss. A system for carbonate resupply 610 and a system 608 for removing depleted $CO_2$ gas are provided.

Example 4

Integrated DIC Production and Biological Synthesis

Figure 7:
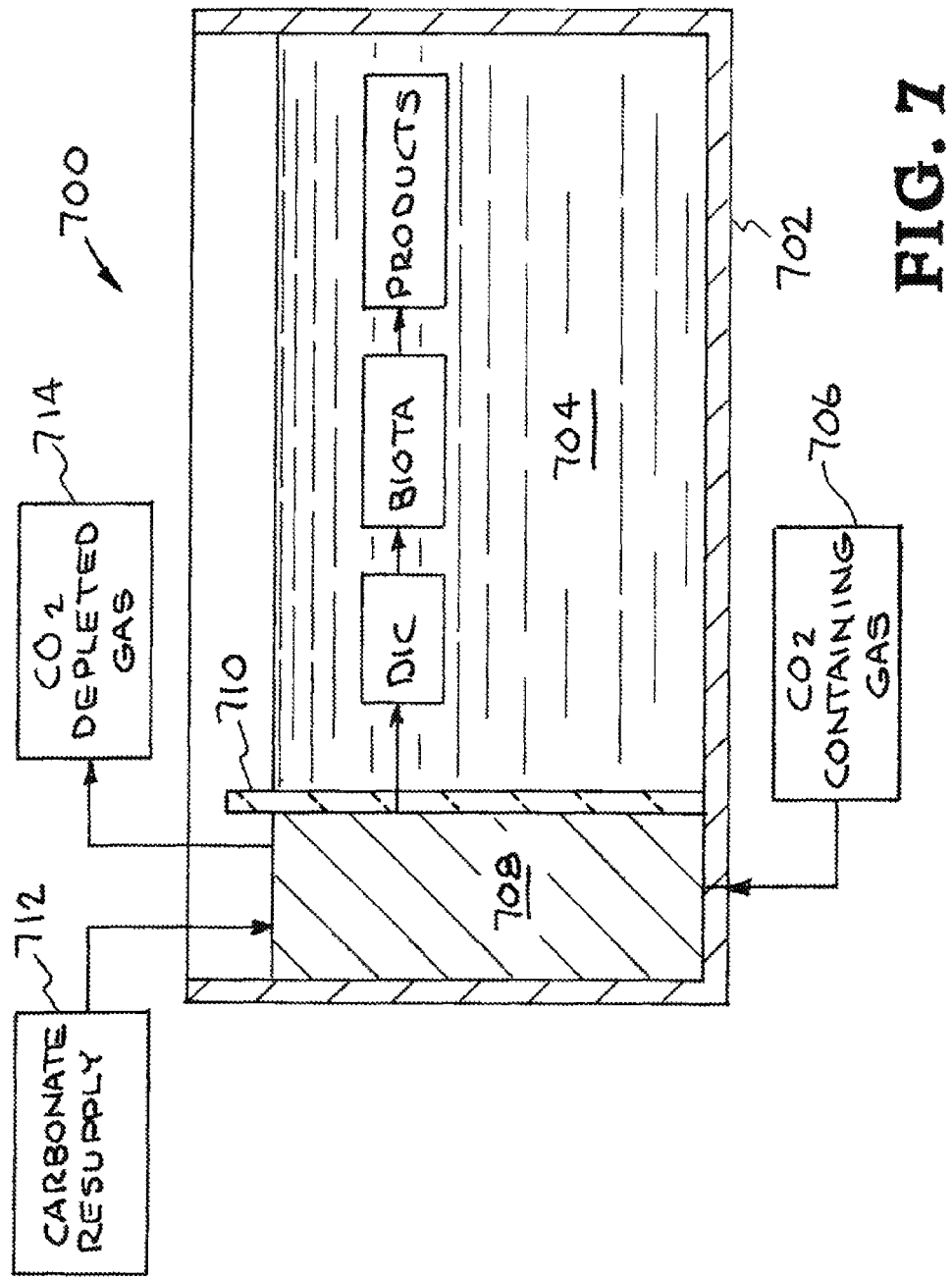
FIG. 7 illustrates an example of DIC production and biosynthesis integrated into a common vessel.

Referring to FIG. 7, a system for integrated DIC production and biosynthesis is illustrated. The system is designated generally by the reference numeral 700. As shown in FIG. 4, gas 706 with elevated $CO_2$ concentration is bubbled through a vertical column of submerged limestone particles 708 that is separated from the main body of a bioreactor 702 by a divider 710 that is porous to the bioreactor's media solution 704. The $CO_2$ partially or fully equilibrates within the submerged particle limestone column producing carbonic acid that in turn reacts with at least some of the limestone, forming calcium bicarbonate in solution. This solution passively diffuses into the main reactor chamber or is mechanically induced to do so via pumps, stirring, or agitation. The now DIC-enriched media is fed to biota within the main chamber that can use the DIC for biological synthesis of products. The subsequently DIC-deplete media is passively or actively returned to the limestone column and the cycle repeated. The rate of media recycling, gas flow, $CO_2$ concentration, and/or quantity of exposed limestone surface area can be used to control DIC concentration relative to DIC utilization or loss. A system for carbonate resupply 712 and a system 714 for removing depleted $CO_2$ gas are provided.

Example 5

Alternative, Integrated DIC Production & Biological Synthesis

Figure 8:
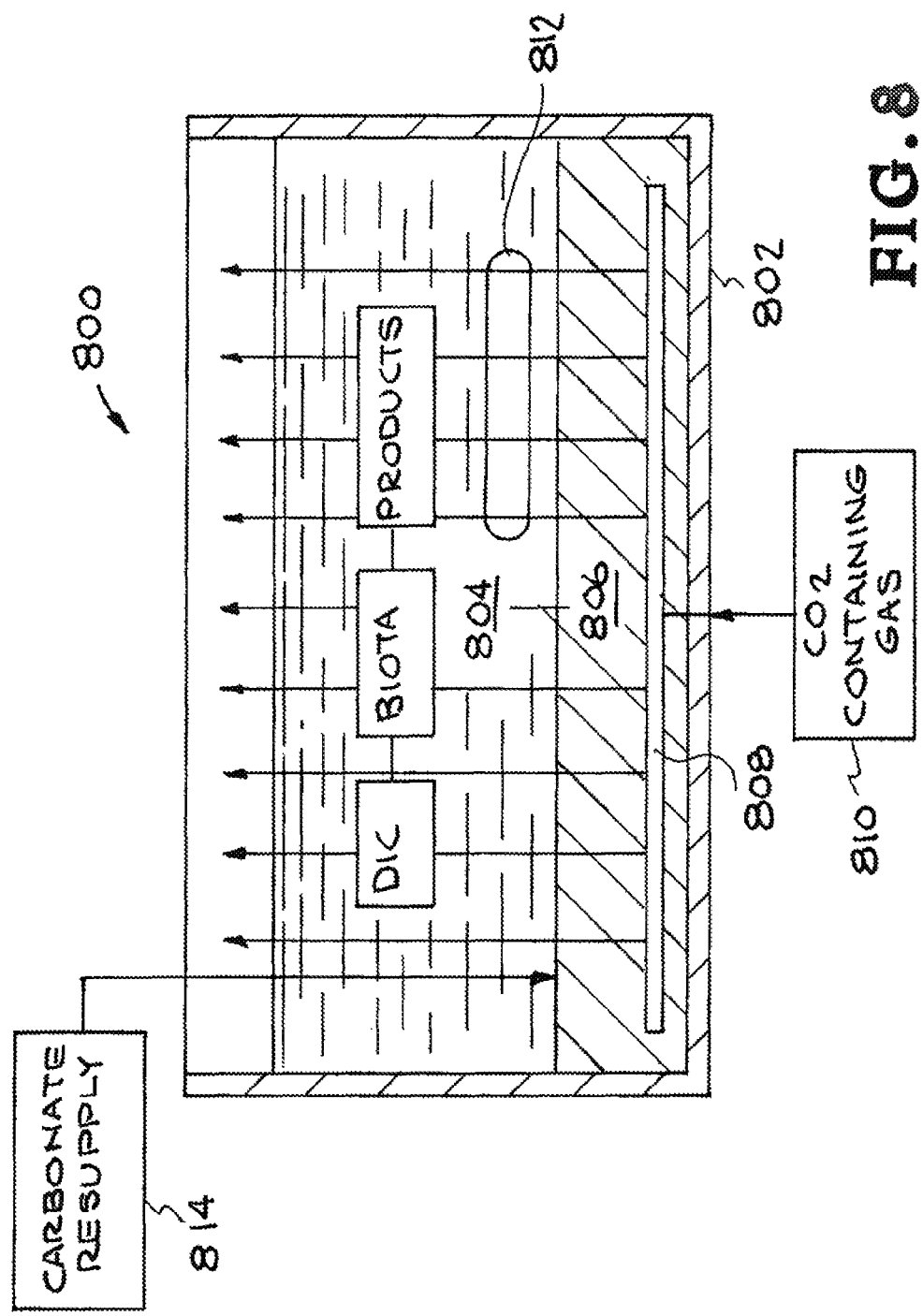
FIG. 8 illustrates an alternative example of DIC production and biosynthesis integrated into a common vessel.

Referring to FIG. 8, a system for alternative, integrated DIC production and biosynthesis is illustrated. The system is designated generally by the reference numeral 800. In the system 800, gas 810 containing $CO_2$ is bubbled through a horizontal layer 806 of crushed limestone residing at the bottom of a bioreactor 802 containing biota and aqueous media 804. The $CO_2$ partially or fully equilibrates with the solution 804 via a gas diffuser 808 within the submerged particle limestone layer 806, locally producing carbonic acid that in turn reacts with and dissolves at least some of the limestone, forming calcium bicarbonate in solution. A system for carbonate resupply 814 is provided. This solution passively diffuses upward into the main portion of the aqueous media 804 and/or is transported 812 by the motion of unreacted gas bubbles emerging from the limestone layer into the main reactor chamber, or is mechanically transported via pumps, stirring, or agitation. The now DIC-enriched media is fed to biota within the bioreactor 802, which can use the DIC for biological synthesis of products. The $CO_2$ concentration, rate of gas flow, and/or quantity of limestone surface area exposed to acidified media can be used to control DIC concentration relative to DIC consumption or loss.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of acidification of mineral carbonate to generate carbon dioxide, for maintaining or increasing the dissolved inorganic carbon concentration in an aqueous media, and for biosynthesis; comprising the steps of:
   providing a carbonate;
   providing an acid;
   providing a first vessel;
   contacting and reacting said carbonate with said acid in said first vessel producing carbon dioxide;
   collecting said carbon dioxide produced in said first vessel;
   providing a second vessel containing the aqueous media and biota; and
   contacting said carbon dioxide with the aqueous media and biota in said second vessel thereby maintaining or increasing the dissolved inorganic carbon concentration in the aqueous media providing growth media for said biota and producing the biosynthesis.

2. The method of acidification of mineral carbonate to generate carbon dioxide, for maintaining or increasing the dissolved inorganic carbon concentration in an aqueous media, and for biosynthesis of claim 1 wherein said carbonate is limestone, calcite, aragonite, dolomite, magnesite, or siderite.

3. The method of acidification of mineral carbonate to generate carbon dioxide, for maintaining or increasing the dissolved inorganic carbon concentration in an aqueous media, and for biosynthesis of claim 1 wherein said acid is sulfuric, nitric, phosphoric, or hydrochloric acid.

4. The method of acidification of mineral carbonate to generate carbon dioxide, for maintaining or increasing the dissolved inorganic carbon concentration in an aqueous media, and for biosynthesis of claim 1 wherein said step of contacting and reacting said carbonate with said acid is achieved within said first vessel wherein said carbonate and said acid can contact and react with each other, producing carbon dioxide that is collected and vented or pumped from said first vessel.

5. The method of acidification of mineral carbonate to generate carbon dioxide, for maintaining or increasing the dissolved inorganic carbon concentration in an aqueous media, and for biosynthesis of claim 4 wherein said vented or pumped carbon dioxide is bubbled, injected, or contacted with the aqueous media, thus partially or fully equilibrating the aqueous media with said carbon dioxide, hence maintaining or increasing said dissolved inorganic carbon concentration in the aqueous media.

6. The method of acidification of mineral carbonate to generate carbon dioxide, for maintaining or increasing the dissolved inorganic carbon concentration in an aqueous media, and for biosynthesis of claim 5 wherein the aqueous media containing said maintained or increased dissolved inorganic carbon concentration is used in biosynthesis of hydrocarbons, fuels, plastics, pharmaceuticals, food, feed, or fiber.

7. A method of acidification of mineral carbonate to generate carbon dioxide, for maintaining or increasing the dissolved inorganic carbon concentration in an aqueous media, and for biosynthesis; comprising the steps of:
  providing a carbonate;
  providing carbonic acid;
  providing a first vessel;
  contacting and reacting said carbonate with said carbonic acid in said first vessel generating carbon dioxide;
  collecting said carbon dioxide generated in said first vessel;
  providing a second vessel containing the aqueous media and biota;
  adding said carbon dioxide to the aqueous media and biota in said second vessel thereby maintaining or increasing the dissolved inorganic carbon concentration in the aqueous media providing growth media for said biota and producing the biosynthesis.

8. The method of acidification of mineral carbonate to generate carbon dioxide, for maintaining or increasing the dissolved inorganic carbon concentration in an aqueous media, and for biosynthesis of claim 7 wherein said carbonate is limestone, calcite, aragonite, dolomite, magnesite, or siderite.

9. The method of acidification of mineral carbonate to generate carbon dioxide, for maintaining or increasing the dissolved inorganic carbon concentration in an aqueous media, and for biosynthesis of claim 7 wherein said carbonate is limestone.

10. The method of acidification of mineral carbonate to generate carbon dioxide, for maintaining or increasing the dissolved inorganic carbon concentration in an aqueous media, and for biosynthesis if claim 7 wherein said carbonate is calcite.

11. The method of acidification of mineral carbonate to generate carbon dioxide, for maintaining or increasing the dissolved inorganic carbon concentration in an aqueous media, and for biosynthesis of claim 7 wherein said carbonate is aragonite.

12. The method of acidification of mineral carbonate to generate carbon dioxide, for maintaining or increasing the dissolved inorganic carbon concentration in an aqueous media, and for biosynthesis of claim 7 wherein said carbonate is dolomite.

13. The method of acidification of mineral carbonate to generate carbon dioxide, for maintaining or increasing the dissolved inorganic carbon concentration in an aqueous media, and for biosynthesis of claim 7 wherein said carbonate is magnesite.

14. An apparatus for acidification of mineral carbonate to generate carbon dioxide, for maintaining or increasing the dissolved inorganic carbon concentration in aqueous media, and for biosynthesis; comprising:
  a carbonate;
  carbonic acid;
  a first vessel in which said carbonate is contacted and reacted with said carbonic acid producing $CO_2$,
  a second vessel containing aqueous media and biota;
  a means of collecting and transporting said $CO_2$ to said second vessel containing aqueous media and biota; and
  a system of contacting and reacting said $CO_2$ with said aqueous media, thereby maintaining or increasing said dissolved inorganic carbon concentration in said aqueous media providing growth media for said biota and producing the biosynthesis.

15. An apparatus for acidification of mineral carbonate to generate carbon dioxide, for maintaining or increasing the dissolved inorganic carbon concentration in aqueous media, and for biosynthesis of claim 14 wherein said carbonate is limestone, calcite, aragonite, dolomite, magnesite, or siderite.

16. An apparatus for acidification of mineral carbonate to generate carbon dioxide, for maintaining or increasing the dissolved inorganic carbon concentration in aqueous media, and for biosynthesis of claim 14 wherein said acid is sulfuric, nitric, phosphoric, or hydrochloric acid.

17. An apparatus for acidification of mineral carbonate to generate carbon dioxide, for maintaining or increasing the dissolved inorganic carbon concentration in aqueous media, and for biosynthesis of claim 14 wherein said carbonate is dolomite.

18. An apparatus for acidification of mineral carbonate to generate carbon dioxide, for maintaining or increasing the dissolved inorganic carbon concentration in aqueous media, and for biosynthesis of claim 14 wherein said carbonate is magnesite.

19. An apparatus for acidification of mineral carbonate to generate carbon dioxide, for maintaining or increasing the dissolved inorganic carbon concentration in aqueous media, and for biosynthesis of claim 14 wherein said carbonated is siderite.

20. An apparatus for acidification of mineral carbonate to generate carbon dioxide, for maintaining or increasing the dissolved inorganic carbon concentration in an aqueous media, and for biosynthesis; comprising:
  a carbonate;
  an acid;
  a first vessel in which said carbonate is contacted and reacted with said acid producing carbon dioxide;
  a second vessel containing the aqueous media, and biota; and
  a system for adding said carbon dioxide to said second vessel for maintaining or increasing the dissolved inorganic carbon concentration in the aqueous media providing growth media for said biota and producing the biosynthesis.

21. The apparatus for acidification of mineral carbonate to generate carbon dioxide, for maintaining or increasing the dissolved inorganic carbon concentration in an aqueous media, and for biosynthesis of claim 20 wherein said carbonate is limestone, calcite, aragonite, dolomite, magnesite, or siderite.

22. The apparatus for acidification of mineral carbonate to generate carbon dioxide, for maintaining or increasing the dissolved inorganic carbon concentration in an aqueous media, and for biosynthesis of claim 20 wherein said carbonate is limestone.

23. The apparatus for acidification of mineral carbonate to generate carbon dioxide, for maintaining or increasing the dissolved inorganic carbon concentration in an aqueous media, and for biosynthesis of claim 20 wherein said carbonate is calcite.

24. The apparatus for acidification of mineral carbonate to generate carbon dioxide, for maintaining or increasing the dissolved inorganic carbon concentration in an aqueous media, and for biosynthesis of claim 20 wherein said carbonate is aragonite.

25. The apparatus for acidification of mineral carbonate to generate carbon dioxide, for maintaining or increasing the dissolved inorganic carbon concentration in an aqueous media, and for biosynthesis of claim 20 wherein said carbonate is dolomite.

26. The apparatus for acidification of mineral carbonate to generate carbon dioxide, for maintaining or increasing the dissolved inorganic carbon concentration in an aqueous media, and for biosynthesis of claim 20 wherein said carbonate is magnesite.

27. The apparatus for acidification of mineral carbonate to generate carbon dioxide, for maintaining or increasing the dissolved inorganic carbon concentration in an aqueous media, and for biosynthesis of claim 20 wherein said carbonate is siderite.

28. The apparatus for acidification of mineral carbonate to generate carbon dioxide, for maintaining or increasing the dissolved inorganic carbon concentration in an aqueous media, and for biosynthesis of claim 20 wherein said maintained or increased dissolved inorganic carbon concentration is further maintained or increased by addition of pure carbon dioxide to said second vessel.

* * * * *